United States Patent [19]

Saferstein et al.

[11] Patent Number: 5,595,735

[45] Date of Patent: Jan. 21, 1997

[54] HEMOSTATIC THROMBIN PASTE COMPOSITION

[75] Inventors: Lowell Saferstein, Edison; Stephen J. Wolf, Neshanic Station, both of N.J.

[73] Assignee: Johnson & Johnson Medical, Inc., Arlington, Tex.

[21] Appl. No.: 528,002

[22] Filed: May 23, 1990

[51] Int. Cl.⁶ .................... A61K 38/48; A61K 35/16; C12N 9/74

[52] U.S. Cl. ............... 424/94.64; 424/529; 424/530; 424/531; 435/214

[58] Field of Search ............ 435/214; 424/94.64, 424/529, 530, 531

[56] References Cited

U.S. PATENT DOCUMENTS

| | | | |
|---|---|---|---|
| 4,363,319 | 12/1982 | Altshuler | 435/214 |
| 4,496,653 | 1/1985 | Lill et al. | 435/7 |
| 4,515,637 | 5/1985 | Cioca et al. | 424/94 |
| 4,696,812 | 10/1987 | Silbering et al. | 424/94.64 |
| 4,752,466 | 6/1988 | Saferstein et al. | 424/46 |
| 5,149,540 | 9/1992 | Kunihiro et al. | 424/489 |
| 5,304,372 | 4/1994 | Michalski et al. | 424/94.64 |
| 5,354,682 | 10/1994 | Kingdon et al. | 435/214 |
| 5,397,704 | 3/1995 | Bocter et al. | 435/214 |
| 5,405,607 | 4/1995 | Epstein | 424/94.64 |

FOREIGN PATENT DOCUMENTS 132842  6/1988  Japan.

OTHER PUBLICATIONS

Remington's Pharmaceutical Sciences, Publishers: Mack Publishing Company, Easton, PA; 1975.

Rotoli et al., "Optimizing and Stabilizing Thrombin Activity", *Chemical Abstracts* 107: 35567r, 1986.

*Primary Examiner*—Chhaya D. Sayala
*Assistant Examiner*—K. Larson

[57] ABSTRACT

A hemostatic paste composition comprising a hemostatic effective amount of thrombin in a polyethylene glycol base which is preferably prepared by admixing an aqueous solution of thrombin and polyethylene glycol and freeze-drying the mixture to remove substantially all of the water to yield a viscous water soluble paste of fine particles of thrombin uniformly dispersed throughout the polyethylene glycol base, and methods of its use to provide hemostasis to a hemorrhaging site of a mammal.

20 Claims, No Drawings

5,595,735

HEMOSTATIC THROMBIN PASTE COMPOSITION

FIELD OF THE INVENTION

This invention relates to hemostatic compositions useful for surgical applications. More particularly, the invention relates to a hemostatic thrombin paste composition comprising a hemostatic effective amount of thrombin in a polyethylene glycol base to form a paste useful as a surgical hemostat.

BACKGROUND OF THE INVENTION

Thrombin is a proteolytic enzyme which is essential for mammalian hemostasis. Thrombin catalyzes the conversion of fibrinogen to fibrin which leads to the formation of blood clots. Thrombin exists in the blood of mammals in the form of prothrombin under normal conditions and when bleeding begins the prothrombin is converted to thrombin which in turn activates the formation of fibrin and consequent blood clots. It is known to initiate hemostasis during surgical procedures by adding an external source of thrombin as a clotting agent to control bleeding at a hemorrhaging site.

Thrombin is generally commercially available in two forms, i.e. dry powder or an aqueous saline solution. In a dry powder form, thrombin particles may be tapped from a container containing the dry powder onto a hemorrhaging site. The dry thrombin is not easily handled and applied during surgery because it is difficult to quickly measure out the desired amount when a hemorrhaging site is discovered. Thrombin used in aqueous saline solutions have the disadvantage of diminishing the potency of the thrombin by dilution. Further, aqueous thrombin solutions are not stable due to the denaturation and autolysis of the thrombin protein in solution. It is therefore an object of the present invention to provide a hemostatically effective, convenient, and storage stable form of thrombin ideally suited for surgical use.

SUMMARY OF THE INVENTION

The foregoing object of providing a convenient to use and stable hemostatic thrombin paste composition has now been accomplished in accordance with the compositions and methods of the present invention. The present invention provides a convenient to use water soluble paste or ointment containing thrombin which can be used in surgery for the control of oozing bleeding from incisions, vascular bleeding, bone incisions etc. or as a topical aid to arrest bleeding from minor cuts, scrapes or burns.

In accordance with purposes of the invention, as embodied and fully described herein, the invention comprises a freeze-dried hemostatic paste composition comprising a hemostatic effective amount of thrombin in a polyethylene glycol base. The polyethylene glycol (PEG) has a molecular weight in the range of about 200 to 6000, preferably blends of various molecular weights of PEG are used. Preferably, thrombin powder is dissolved in a mixture of water and polyethylene glycol and the mixture is dried, preferably, freeze-dried to remove the water leaving the particles of thrombin uniformly dispersed in the PEG base. The thrombin paste composition comprises from about 100 to 10,000 and preferably 500–2,000 units of thrombin per gram of paste.

The invention also comprises a process for preparing a viscous water soluble thrombin paste composition comprising the steps of: admixing an aqueous solution of thrombin and polyethylene glycol having a molecular weight range of from about 200 to 6000 preferably blends of various molecular weights of PEG are used; and freeze-drying the mixture to remove substantially all of the water to yield a viscous water soluble paste of thrombin and PEG. Preferably, the PEG is a blend having an average molecular weight of in the range of 500 to 1,000, preferably a 1:1 blend of PEG 300 MW and 1500 MW.

The invention further comprises a method for reducing bleeding at a hemorrhaging site by applying a thrombin paste composition comprising a hemostatic effective amount of thrombin in a base comprising polyethylene glycol to the hemorrhaging site of a mammal. The thrombin may be applied in combination with a fibrous gauze material or by itself in paste form to the hemorrhaging site.

DETAILED DESCRIPTION OF THE PREFERRED EMBODIMENTS OF HTE INVENTION

Reference will now be made in detail to preferred embodiments of the invention, examples of which are illustrated in the following examples section.

The hemostatic thrombin paste composition of the present invention provides convenient ready to use hemostatic effective amounts of thrombin for application to a hemorrhaging site. The thrombin composition is homogeneously dispersed throughout the polyethylene glycol-paste composition and remains storage stable under refrigeration until it is ready for use.

The ready to use paste form of the present invention is advantageous over saline solution forms of thrombin which must be reconstituted from dry thrombin prior to use. Additionally, thrombin in solution has a low viscosity and a low potency due to its dilute nature. Aqueous solution of thrombin is frequently applied in conjunction with and absorbed on a gelatin.sponge, gauze or collagen hemostat because of its low viscosity. The thrombin paste of the present invention has a viscosity and potency which is high enough to permit its hemostatic effective use by a surgeon by dipping of a gloved finger into the thrombin paste and placing the paste over the bleeding site.

The thrombin paste may also be used in conjunction with a gelatin sponge, gauze or collagen material by either coating such material as a substrate with the thrombin paste and applying it to the hemorrhaging site or first applying the thrombin paste to a hemorrhaging site and placing the gelatin sponge, gauze or collagen on top of the thrombin paste and applying pressure thereto.

The thrombin paste composition requires no pre-preparation, it is non-toxic and absorbable by a mammalian body. It can be supplied in a sterile convenient to use delivery system such as a paste tube or a paste jar. The thrombin paste composition is readily dissolvable due to the water soluble nature of the polyethylene glycol carrier.

In accordance with the purposes of the invention, as embodied and fully described herein, the invention comprises a mixture of polyethylene glycols and a hemostatic amount of thrombin. Polyethylene glycol is a polymer made by the controlled polymerization of ethylene oxide. It can be produced within a fairly narrow molecular weight range and several grades are commercially available. The low molecular weight grades are liquids, the intermediate grades are semi-solids and the high molecular weight grades of polyethylene glycols are solids. All the grades dissolve in water. PEG products because of their unusual combination of properties: water solubility; lubricity; blandness; low toxicity; stability; solvent action; nonvolatility; and availability in a range of molecular weights, varying from viscous liquids to hard, waxy solids at room temperature; find a very wide range of application in which they serve many functions in many products. In addition to their water solubility, blandness and solvent action, PEG based products spread easily, produce a pleasant, nongreasy feel on the skin, and are tolerant of body fluids. This invention takes advantage of these properties of PEG bases to produce a homstatic ointment containing thrombin to aid in the arrest of bleeding.

Grades of polyethylene glycol can be combined with one another to produce unique properties. For example, PEG 1500, a solid at room temperature, while not soluble in liquid PEG 300 at room temperature may be combined together and heated above the melting point of the higher melting glycol (i.e. PEG 1500) to form a solution. For example, PEG 300 which is a liquid, is mixed with an equal weight of PEG 1500, a solid melting at 43° C., and the two heated together at or above the melting point of PEG 1500 they liquify to a homogeneous solution, and when that solution is cooled to room temperature, it forms a smooth, soft paste. This paste is water soluble, and sufficiently yielding to spread readily on tissue or skin. This paste can be likened to petrolatum except that petrolatum is hydrocarbon based and not water soluble. This paste can also be formed by combining equal weights of the PEG 1500 and the PEG 300 in a common solvent such as water or methyl alcohol to form a solution. Removal of the solvent by evaporation or sublimation will produce a paste composed of a blend of these polyethylene glycols.

The present invention preferably utilized but is not limited to a 1:1 ratio blend of PEG 1500 and 300 which possesses a unique petrolatum like qualities. The 1:1 blend is commercially available from several companies, for example, Union Carbide Co. commercially markets "CARBOWAX 540." This most preferred ratio of polyethylene glycols can be altered to a degree from the normal 1:1 ratio of polyethylene glycol 1500: polyethylene glycol 300 to give a paste with slightly firmer or softer feel depending on the ratio of glycols. For this invention preferred formulations containing up to 70% polyethylene glycol 1500 with 30% polyethylene glycol 300 are used. Blends with higher than 70% by weight of polyethylene glycol 1500 are not preferred because they are too hard and do not spread on soft tissue readily. Blends can also be prepared with as much as 70% by weight of polyethylene glycol 300 and 30% by weight of polyethylene glycol 1500. Blends with more than 70% polyethylene glycol 300 are too thin and liquid-like to be useful for this application.

Any of the above mentioned blends of polyethylene glycol can be employed as the base for an ointment containing thrombin. When thrombin is incorporated into any of these polyethylene glycol blends, a therapeutic ointment or paste is produced which can be applied to a cut, bleeding wound, incision, to effect rapid hemostasis through the release of thrombin.

For the paste of the invention to work effectively as a hemostat, the ratio of thrombin to polyethylene glycols can be 100 units of thrombin per gram of paste up to 10,000 units of thrombin per gram of paste. Most preferably it is 500–2,000 units of thrombin per gram of paste.

The source of thrombin can be any mammalian species but most preferably are bovine, porcine and human. The ointment or paste may also contain up to 10% by weight glycerol or propylene glycol. Other components can include up to 0.1% antibacterial agent, plasma proteins such as albumin, pH adjusters such as sodium bicarbonate, and antifibrinolytic agents such as epsilon amino caproic acid which prevents the fibrin clot from dissolving too quickly.

The most preferred method of preparing the paste is to mix the thrombin and the polyethylene glycols together with water using no less water than 10 times the weight of paste. The water dissolves all the components and forms a homogeneous solution. The solution is then frozen and lyophilized under high vacuum to evaporate the water while in the frozen state. After the water is fully removed, the mixture is brought up to room temperature producing a soft, smooth, water free paste of polyethylene glycols with thrombin distributed uniformly throughout. A thrombin paste prepared by this technique will show 80% of the original thrombin activity remaining after 900 days at 4° C.

The thrombin paste can also be prepared by physically blending the dry thrombin powder into the soft polyethylene glycol paste and mixing well to uniformly distribute the thrombin particles throughout the paste. The paste can be slightly heated 30°–40° C. to further soften the base and aid in mixing but care must be taken not to overheat the paste and cause the thrombin to lose its activity.

In preferred embodiments the thrombin composition of the invention is prepared by first admixing a hemostatic effective amount of thrombin with polyethylene glycol. The thrombin is an aqueous solution as it is admixed with the polyethylene glycol and must be freeze-dried to provide a smooth non-gritty paste. Mixing of powdered thrombin with polyethylene glycol will give a lumpy paste as will mixing an aqueous solution of thrombin with polyethylene glycol and air drying. Freeze-drying the admixture of aqueous thrombin and polyethylene glycol is required to yield very small particles of thrombin homogeneously dispersed throughout the composition mixture without loss of enzyme activity.

The polyethylene glycol that is used has an average molecular weight range of from about 500 to 1000 or more preferably about 900. Polyethylene glycol in these ranges have a viscosity which is most desirable for producing a product which may be handled easily by a surgeon during surgical procedures where a hemostat is necessary. The viscosity achieved also permits easy dispensing of the thrombin paste from a paste tube by squeezing out the desired amount onto a gloved finger of the surgeon or on to a substrate such as a gelatin sponge, gauze or collagen material or for dispensing from a paste jar by dipping of a gloved finger therein.

EXAMPLES

The invention will now be illustrated by examples. The examples are not intended to be limiting of the scope of the present invention but read in conjunction with the detailed and general description above to provide further understanding of the present invention and an outline of a process for preparing the compositions of the invention and practicing the methods of the invention.

The following examples represent preferred embodiments of the compositions, processes and methods of the invention. The following examples will illustrate the process of making the paste, monitoring its stability and measuring its hemostatic efficacy.

EXAMPLE 1

PREPARATION OF A 50% PEG 1500:50% PEG 300 THROMBIN PASTE.

Five grams each of polyethylene glycol 300 and polyethylene glycol 1500 were added to 100 grams of water and the pH adjusted to 6.6 with a few drops of 1% sodium bicarbonate solution. Ten thousand units of bovine thrombin from GenTrac Inc. were dissolved in 10 ml. of isotonic saline and added the polyethylene glycol solution. The resulting solution was placed in a tray and frozen at −20° C. on the shelf of a freeze dryer. When the solution was fully frozen the vacuum was turned on and the temperature was raised to 20° C. The water present was removed during a 24 hour period. After the water was fully removed, the temperature was brought up to 35° C. and held there for 1 hour. The tray was then removed from the lyophilizer and the paste removed and assayed for thrombin activity by fibrometry. The activity indicated that the blend contained 980 units of thrombin per gram of paste. Theoretical would be 1,000 units of thrombin per gram of paste. The paste was placed in a jar and kept in a refrigerator at 4° C. for 900 days. The activity of the thrombin after 900 days was 80% of the original activity indicating good stability at this temperature.

EXAMPLE 2

PREPARATION OF A 30% PEG 1500:70% PEG 300 THROMBIN PASTE.

2.04 grams of polyethylene glycol 1500 and 4.76 grams of polyethylene glycol 300 were added to 75 ml. of water and the pH adjusted to 6.0 with a few drops of 5% sodium bicarbonate solution. This ratio is 70% by weight polyethylene glycol 300 and 30% by weight polyethylene glycol 1500. Dissolve 10,000 units of thrombin in 10 ml of distilled water and add it to the polyethylene glycol solution. Place the solution in a tray and freeze it at −20° C. Place the frozen solution in a freeze dryer and turn on the vacuum and raise the temperature up to 30° C. for 1 hour to remove the water. At the end of this time the soft paste is removed from the tray and assayed for thrombin activity. The fibrometry assay shows 1400 units of thrombin per gram of paste. The paste was placed in a jar and put into a refrigerator at 4° C. Assay of this paste 775 days later showed 87% of the thrombin activity remaining.

EXAMPLE 3

EFFICACY OF THROMBIN PASTE.

The thrombin paste as made in Example 2 was tested for hemostasis efficacy using a 1.5 cm long by 3 mm deep incision in the spleen of a swine. One gram of paste was placed on the bleeding incision and held down with light pressure using a 4×4 inch gauze sponge. The wound was observed every 30 seconds for evidence of bleeding. The average bleeding time on five wounds for the thrombin paste was 2.5 minutes. When the paste alone without thrombin was tested in the same model, it showed a bleeding time of 8.3 minutes and the gauze alone bled for 10 minutes. The superior efficacy of the thrombin paste is demonstrated thereby. Although the paste is water soluble it was found to be slow to dissolve in water or in blood. The thrombin paste acts initially as an impenetrable barrier for the blood, but as the paste slowly gets eroded away, it begins to dissolve and in so doing liberates the thrombin which brings about coagulation of the blood.

EXAMPLE 4

PREPARATION OF A THROMBIN PASTE CONTAINING 7.6% BY WEIGHT GLYCEROL.

Into a beaker containing 100 ml. of water was placed 6 grams of "CARBOWAX 540" brand polyethylene glycol and 0.5 grams of glycerol. Five thousand units of bovine thrombin dissolved in 5 ml of water was added this solution and the pH adjusted to 6.0 with a few drops of 5% sodium bicarbonate. The entire mixture was added to a tray and frozen at −20° C. on a shelf of a freeze dryer. When the entire solution was fully frozen, the vacuum was turned on and the frozen solution lyophilized for 24 hours. After all the water was removed the shelf temperature was raised to 30° C. and held there for 1 hour. After 1 hour the soft paste was removed from the tray and assayed for thrombin activity by fibrometry. The paste was found to have 720 units of thrombin per gram. Theoretical yield would be 770 units of thrombin per gram of paste. This paste was soft and readily spreadable on skin or soft tissue. When 1 gram was applied to a 1.5 cm. splenic incision it stopped bleeding in 3 minutes compared to 9 minutes for the paste without thrombin.

EXAMPLE 5

THROMBIN OINTMENT BY DRY BLENDING THROMBIN INTO CARBOWAX 540.

Nine grams of "CARBOWAX 540" brand polyethylene glycol was placed in a bottle and 10,000 units of powdered thrombin was added to the polyethylene glycol. The thrombin was stirred into a paste with a stirrer for ten minutes by heating to 40° C. at which temperature the polyethylene glycol liquefied and mixed readily with the thrombin which does not dissolve but becomes distributed throughout. Upon cooling to room temperature an ointment is produced with thrombin incorporated throughout. This paste showed 40% of the original thrombin activity after 60 days at 4° C. The scope of the present invention is not limited by the description, examples and suggested uses herein and modifications can be made without departing from the spirit of the invention. For example, other applications of the thrombin paste composition, for example, first aid treatment of wounds are possible.

Application of the compositions and methods of the present invention for medical and surgical uses can be accomplished by any suitable surgical and medical method and technique as is presently or prospectively know to those skilled in the art. Thus it is intended that the present invention cover the modifications and variations of this invention provided they come within the scope of the appended claims and their equivalents.

What is claimed is:

1. An anhydrous hemostatic paste composition comprising a hemostatically effective amount of thrombin uniformly dispersed in a polyethylene glycol base and wherein the paste composition is freeze-dried.

2. The composition of claim 1 wherein the average molecular weight of the polyethylene glycol base is between about 500 and 1000.

3. The composition according to claim 1 wherein the average molecular weight of the polyethylene glycol is about 900.

4. The composition of claim 2 wherein the concentration of thrombin is about 100 to 10,000 units per gram of the paste composition.

5. The composition of claim 2 wherein the concentration of thrombin is about 500 to 2,000 units per gram of the paste composition.

6. The composition of claim 3 wherein the concentration of thrombin is about 500 to 2,000 units per gram of the paste composition.

7. The composition according to claim 1 which exhibits 80% of the original thrombin activity after being stored at 4° C. for 900 days.

8. A process for preparing a viscous water soluble thrombin paste composition comprising the following steps:

(a) mixing an aqueous solution of a hemostatically effective amount of thrombin and polyethylene glycol, wherein the polyethylene glycol has an average molecular weight of about 500 to 1,000; and (b) drying the mixture to remove substantially all of the water to yield a viscous water soluble thrombin paste composition.

9. The process of claim 8 wherein the average molecular weight at the polyethylene glycol is about 900.

10. The process of claim 8 wherein the drying step is accomplished by freeze-drying.

11. The process of claim 8 wherein the amount of water in the mixture, prior to the step of removing the water, is at least ten times the weight of the paste after the drying step.

12. The process of claim 10 wherein the concentration of thrombin is about 100 to 10,000 units per gram of the paste composition.

13. The thrombin paste composition produced by the process of claim 12.

14. The process of claim 12 wherein the average molecular weight of the polyethylene glycol is about 900.

15. The process of claim 14 wherein the concentration of thrombin is about 100 to 10,000 units per gram of the paste composition.

16. The process of claim 14 wherein the concentration of thrombin is about 500 to 1,000 units per gram of the paste composition.

17. A hemostatic method for reducing bleeding at a hemorrhaging site in a mammal comprising the following steps:

(a) forming an anhydrous hemostatic paste by mixing a hemostatically effective amount of thrombin, water and polyethylene glycol to form a mixture;

(b) drying the mixture to remove the water to produce the anhydrous hemostatic paste; and (c) applying an amount of the anhydrous hemostatic paste effective to reduce bleeding to the hemorrhaging site of the mammal.

18. The method of claim 17 further comprising applying the anhydrous hemostatic paste to a fibrous gauze after step (b).

19. The method of claim 17 wherein the average molecular weight of the polyethylene glycol is from about 500 to 1,000.

20. The method of claim 19 wherein the water is removed by lyophilization.

* * * * *